(12) United States Patent
Krawiec (10) Patent No.: US 12,279,970 B2
(45) Date of Patent: Apr. 22, 2025

(54) ARTICULATING GRAFT DELIVERY

(71) Applicant: GLOBUS MEDICAL, INC., Audubon, PA (US)

(72) Inventor: Catherine Krawiec, Conshohocken, PA (US)

(73) Assignee: Globus Medical Inc., Audubon, PA (US)

( * ) Notice: Subject to any disclaimer, the term of this patent is extended or adjusted under 35 U.S.C. 154(b) by 365 days.

(21) Appl. No.: 17/837,247

(22) Filed: Jun. 10, 2022

(65) Prior Publication Data
US 2023/0397997 A1 Dec. 14, 2023

(51) Int. Cl.
*A61F 2/46* (2006.01)
(52) U.S. Cl.
CPC .................. *A61F 2/4601* (2013.01)
(58) Field of Classification Search
CPC ..................................... A61F 2/4601
See application file for complete search history.

(56) References Cited

U.S. PATENT DOCUMENTS

| | | | |
|---|---|---|---|
| 2004/0044412 A1* | 3/2004 | Lambrecht | A61B 5/1076 623/17.16 |
| 2006/0142732 A1* | 6/2006 | Karmarkar | A61M 25/0138 604/95.01 |
| 2015/0045892 A1* | 2/2015 | Lynn | A61B 17/1671 623/17.16 |
| 2016/0206853 A1* | 7/2016 | Bolduc | A61M 25/0136 |
| 2022/0265964 A1* | 8/2022 | Asami | A61M 25/0662 |
| 2023/0397929 A1* | 12/2023 | Ricotti | A61B 17/3421 |
| 2024/0237967 A1* | 7/2024 | Steinberg | A61B 8/08 |

* cited by examiner

*Primary Examiner* — Tessa M Matthews (57) ABSTRACT

A graft delivery device includes a graft delivery tube having a main passage for delivering graft material to a surgical implant inserted between adjacent vertebrae of a spine. The graft delivery tube includes an articulating portion proximate an output end of the graft delivery tube. The graft delivery device also includes a pusher device slidable along the main passage to drive graft material through the main passage toward the output end of the graft delivery tube, an actuation wire extending axially through at least the articulating portion of the graft delivery tube, and an actuation device connected to the actuation wire. The actuation device is actuatable to pull the actuation wire. Moreover, pulling the actuation wire bends the articulating portion of the graft delivery tube and positions the output end proximate the surgical implant.

18 Claims, 10 Drawing Sheets

ARTICULATING GRAFT DELIVERY

BACKGROUND

Intervertebral implants (e.g., interbody spacers or cages) are used for fusing adjacent vertebrae of the spine. The implants are inserted between adjacent vertebra of the spine. Generally, the implants include cavities that are oriented axially with respect to the long axis of the spine such that bone may grow through the cavity. Eventually, the bone growth through the implant fuses the adjacent vertebrae to each other. Some implants and their corresponding inserters (e.g., surgical implant inserters) are designed such that autogenous or allograft material (e.g., graft material) may be delivered through the inserter and into the cavity of the implant. Unfortunately, certain implant and/or inserter designs include features that block delivery of the graft material through the inserter and into the cavity of the implant. Failing to deliver graft material to these implants may reduce their effectiveness by reducing implant success rates, as well as increasing recovery times for patients.

BRIEF DESCRIPTION OF THE DRAWINGS

These drawings illustrate certain aspects of some of the embodiments of the present invention and should not be used to limit or define the invention.

DETAILED DESCRIPTION

It is to be understood that the present disclosure is not limited to particular systems, devices, and/or methods, which may, of course, vary. It is also to be understood that the terminology used herein is for the purpose of describing particular embodiments only and is not intended to be limiting. All numbers and ranges disclosed herein may vary by some amount. Whenever a numerical range with a lower limit and an upper limit is disclosed, any number and any included range falling within the range are specifically disclosed. Although individual embodiments are discussed herein, the invention covers all combinations of all those embodiments. As used herein, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected. If there is any conflict in the usages of a word or term in this specification and one or more patent or other documents that may be incorporated herein by reference, the definitions that are consistent with this specification should be adopted for the purposes of understanding this invention.

Aspects of the present disclosure include a surgical implant system and a graft delivery device usable with the surgical implant system to facilitate delivery of material (e.g., graft material) in performing surgical procedures. In such surgical procedures, any of a variety of materials can be delivered into a patient. Among these materials include biological graft material such as autograft, allograft and synthetic material, as well as different types of cements. These materials can be delivered, for example, during a surgical procedure, such as a spinal fusion procedure. In some procedures, a spacer or cage can be delivered into a disc space, along with biological material to assist in fusion and bone growth. Corresponding inserters (e.g., surgical implant inserters) are designed such that the graft material may be delivered through the inserter and into a cavity of the spacer or the cage. The disclosure in any of its various configurations may include a graft delivery device that may deliver the graft material to the spacer or cage (e.g., the implant). Desirably, the disclosure include features that, unlike prior solutions, avoid blocking delivery of the graft material and actually facilitate the delivery of graft material into the cavity of the implant. Ensuring the delivery of graft material to these implants may improve their effectiveness by greatly improving implant success rates, as well as reducing recovery times for patients.

Figure 1:
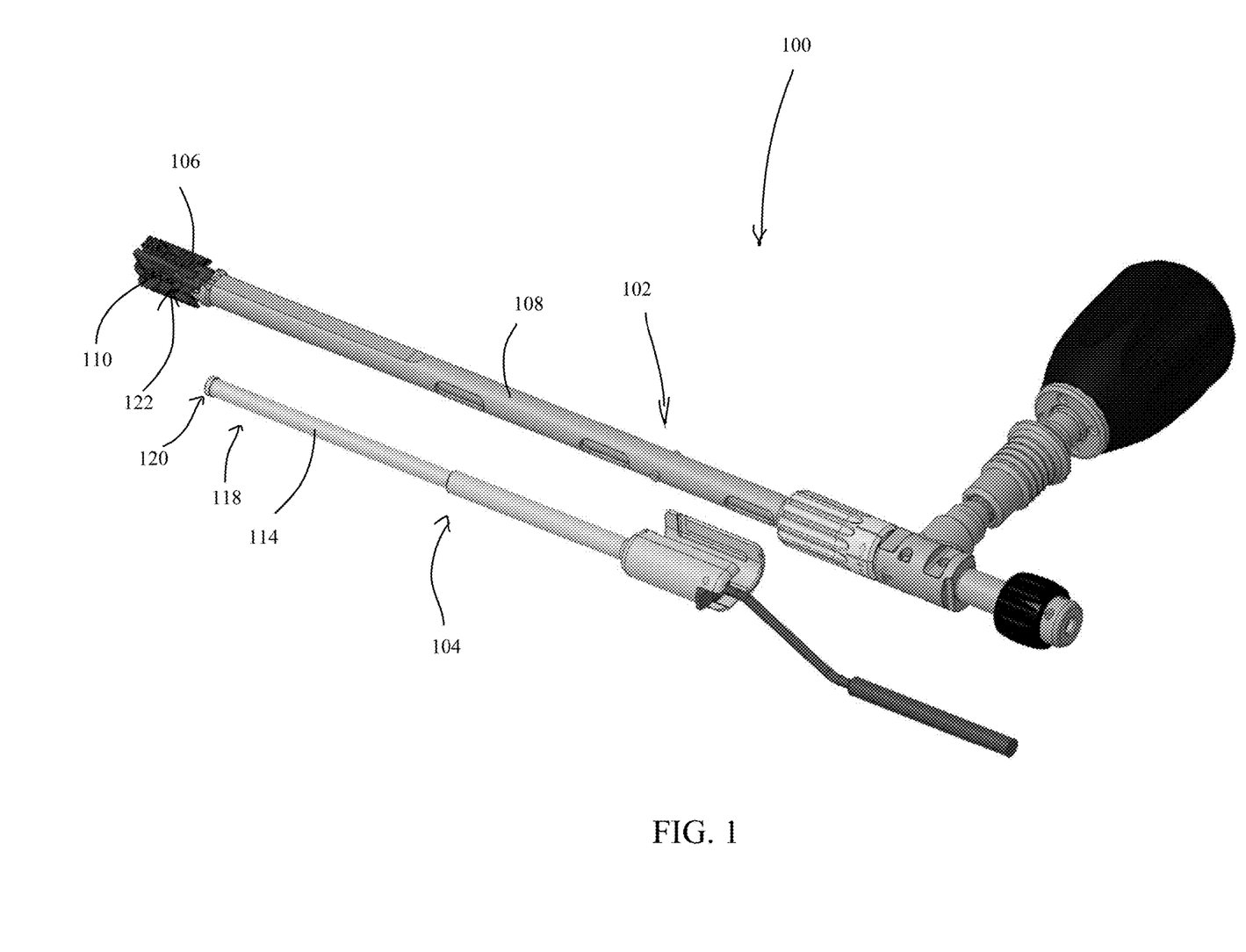
FIG. 1 is a perspective view of a surgical implant system having a surgical implant inserter and a graft delivery device.

Referring now to the drawings, FIG. 1 is a perspective view of an example configuration of a surgical implant system 100 having a surgical implant inserter 102 and a graft delivery device 104. During a surgical procedure, a surgical implant 106 (e.g., an interbody spacer or cage) is attached to an end of the surgical implant inserter 102, which may include an extended body 108 for minimally invasive surgery. The surgical implant inserter 102 may pass the surgical implant 106 through a small incision and insert the surgical implant 106 between adjacent vertebra of the spine. The surgical implant 106 may include a cavity 110 for receiving graft material 112 (shown in FIG. 3), such as autograft, allograft, and synthetic material, which may assist in spinal fusion and bone growth. In one embodiment, the surgical implant 106 is an expandable intervertebral spacer having a first and second endplate that expands when actuated by an actuation device.

The surgical implant system 100 also includes the graft delivery device 104, which is couplable to the surgical implant inserter 102. During a surgical procedure, the graft delivery device 104 may be coupled to the surgical implant inserter 102. Coupling the graft delivery device 104 to the surgical implant inserter 102 may assist with aligning and positioning the graft delivery device 104. However, the graft delivery device 104 may alternatively deliver the graft material without coupling to the surgical implant inserter 102. The graft delivery device 104 includes a graft delivery tube 114 having a main passage 116 (shown in FIGS. 3A and 3C) for delivering graft material to a surgical implant 106 inserted between adjacent vertebrae of a spine. The graft delivery tube 114 may also include or accommodate an articulating portion 118 proximate an output end 120 of the graft delivery tube 114 that is capable of articulating (as better seen in FIG. 2), such that the graft delivery tube 114 may deliver the graft material 112 through a side 122 of the surgical implant 106. As such, the graft delivery device 104 may deliver the graft material 112 while the surgical implant inserter 102 is still coupled to the surgical implant 106.

Figure 2:
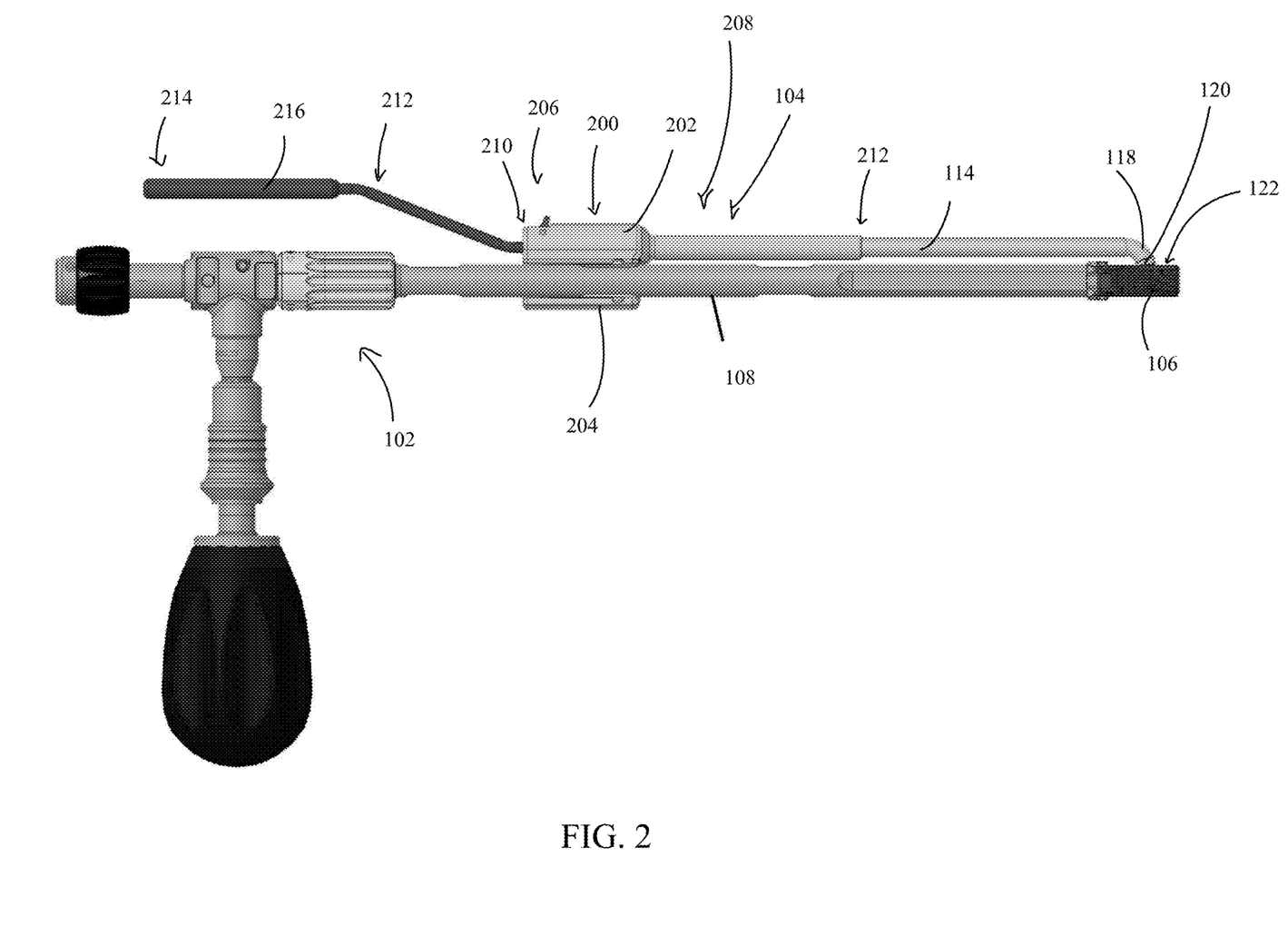
FIG. 2 is a side view of the graft delivery device coupled to the surgical implant inserter.

FIG. 2 is a side view of the graft delivery device 104 coupled to the surgical implant inserter 102. As illustrated, the graft delivery device 104 may include an attachment device 200 for coupling the graft delivery device 104 to the surgical implant inserter 102. The attachment device 200 may have a main body portion 202 with a coupling portion 204 (which may be resemble or embody an arm in some configurations) that may at least partially encircle the extended body 108 of the surgical implant inserter 102 as shown, for slidably coupling the graft delivery device 104 to the surgical implant inserter 102. The coupling portion 204 may slide along the graft delivery device 104 from an entry position to a delivery position. The side view of FIG. 2 shows the articulating portion 180 in an articulated (e.g., bent) position. As set forth in greater detail below, sliding the graft delivery device 104 from the entry position to the delivery position may cause the articulating portion 118 to articulate (e.g., to bend) and position an output end 120 of the graft delivery tube 114 proximate the side 122 of the surgical implant 106 such that the graft delivery tube 114 may deliver the graft material 112 (discussed generally in connection with FIGS. 3A-3D) through the side 122 of the surgical implant 106.

Moreover, the main body portion 202 (or, specifically, the coupling portion 204) of the attachment device 200 may be disposed around the graft delivery tube 114 proximate an input end 206 of the graft delivery tube 114. However, the main body portion 202 may be disposed around any suitable portion of the graft delivery tube 114. In the illustrated, the main body portion 202 is disposed around an upper portion 208 of the graft delivery tube 114. The upper portion 208 extends between a proximal end 210 and a middle 212 of the graft delivery tube 114. The upper portion 208 of the graft delivery tube 114 may be substantially rigid, such that it does not flex appreciably and provides structural support to other features during use. Further, the main body portion 202 may be rigidly secured to the graft delivery tube 114 such that the main body portion 202 is rotationally and slidably fixed with respect to the graft delivery tube 114.

The graft delivery device 104 may also include a pusher device 212 disposed at least partially within the main passage 116 (shown in FIG. 3). The pusher device 212 may be actuatable to drive the graft material 112 through the main passage 116 of the graft delivery tube 114 and into the surgical implant 106. In the illustrated embodiment, a proximal end 214 of the pusher device 212 extends out of the proximal end 210 of the graft delivery tube 114. The proximal end 214 of the pusher device 212 may include a handle 216 as illustrated. The handle 216 having a larger diameter than other portions of the pusher device 212 for ease of handling. Alternatively, the pusher device 212 may operate without the handle 216.

Figure 3A:
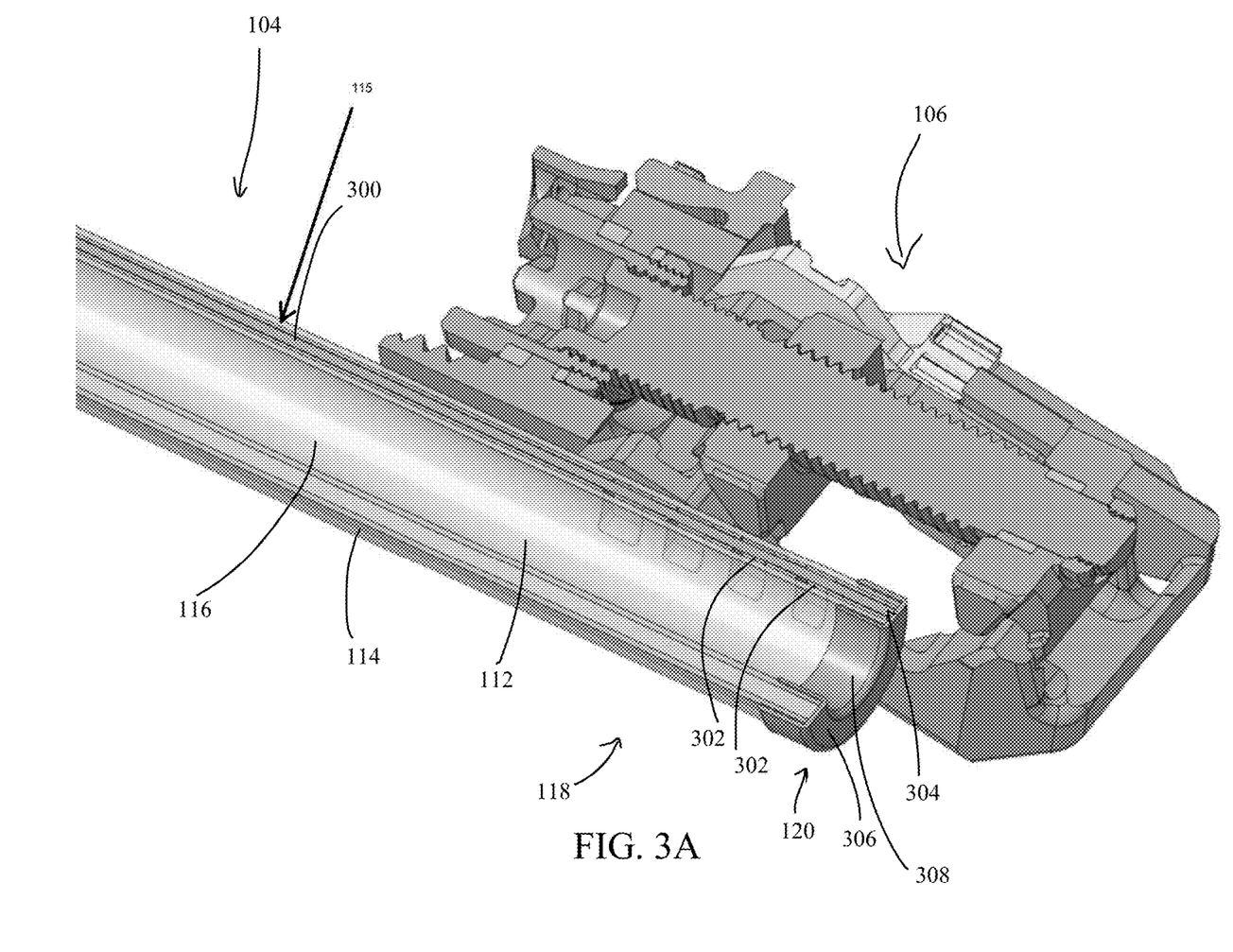
FIG. 3A is a cutaway view of the graft delivery device with the graft delivery tube in the entry position.

FIGS. 3A-3D are respective cutaway views of the graft delivery device 104 actuating to articulate and couple with a surgical implant 106 and deliver graft material 112. In particular, FIG. 3A is a cutaway view of the graft delivery device 104 with the graft delivery tube 114 in the entry position. In the entry position, the articulating portion 118 of the graft delivery tube 114 is straight (e.g., not articulated). As set forth above, the graft delivery tube 114 has the main passage 116 for delivering the graft material 112 to the surgical implant 106 inserted between adjacent vertebrae of a spine, as well as the articulating portion 118 proximate the output end 120 of the graft delivery tube 114. The graft delivery tube 114 further includes the pusher device 212 (see, e.g., FIGS. 3C and 3D) slidable along the main passage 116 to drive the graft material 112 through the main passage 116 toward the output end 120 of the graft delivery tube 114.

Moreover, the graft delivery tube 114 includes an actuation wire 300 extending axially along a wire passage 115 of the graft delivery tube 114, which may be substantially parallel to the main passage 116 along at least a portion of the graft delivery tube. The actuation wire 300 extends along the wire passage 115 through at least the articulating portion 118 of the graft delivery tube 114. Further, the articulating portion 118 may include a plurality of articulation slits 302 formed in the articulating portion 118 of the graft delivery tube 114 to control an amount of bending of the articulating portion 118. The actuation wire 300 may extend through the plurality of articulation slits 302. However, in alternative configurations the actuation wire 300 may extend through any suitable portion of the graft delivery tube 114 that will allow the actuation wire 300 to effectuate the articulation. As illustrated in the illustrated example, a distal end 304 (e.g., first end) of the actuation wire 300 may be secured proximate the output end 120 of the graft delivery tube 114. In the illustrated embodiment, the actuation wire 300 is secured via an end cap 306 disposed at the output end 120 of the graft delivery tube 114. However, any suitable fastener may be used to secure the actuation wire 300 proximate the output end 120. Moreover, the end cap 306 includes a hollow center portion 308 such that the graft material 112 may pass through the end cap 306 to the surgical implant 106 during operation.

Figure 3B:
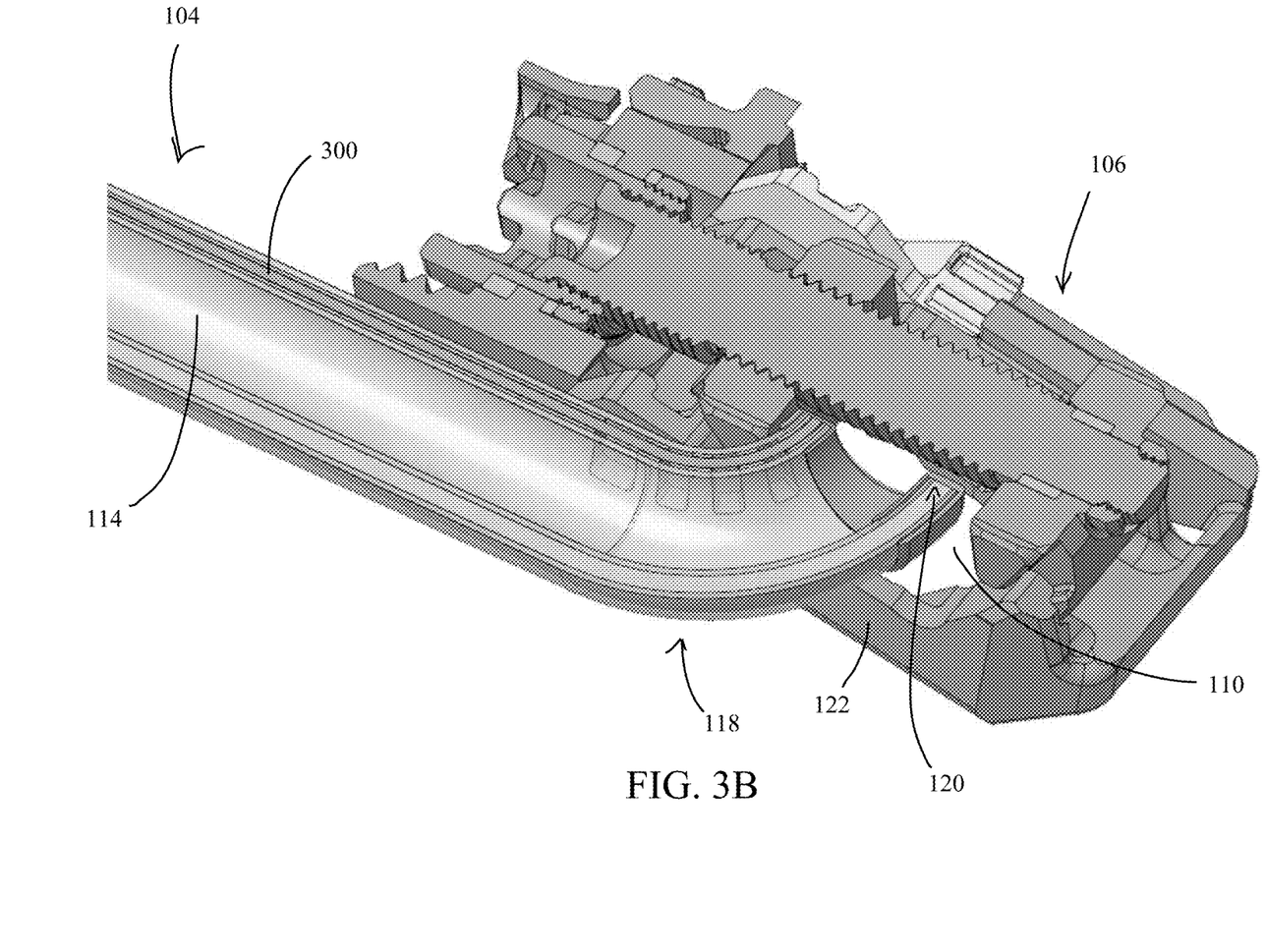
FIG. 3B is a cutaway view of the graft delivery device with the graft delivery tube in an articulated position.

FIG. 3B is a cutaway view of the graft delivery device 104 with the graft delivery tube 114 in an articulated position (e.g., the delivery position). The graft delivery device 104 includes an actuation device 310 (shown in FIGS. 6-7) configured to bend the articulating portion 118 to transition the graft delivery tube 114 from the entry position to the articulated position. As set forth in greater detail below, the actuation device 310 is connected to the actuation wire 300 and is actuatable to pull the actuation wire 300. Pulling the actuation wire 300 bends the articulating portion 118 of the graft delivery tube 114 from the entry position to the articulated position. Further, pulling the actuation wire 300 may move the output end 120 of the graft delivery tube 114 to a position proximate the surgical implant 106. As illustrated, the output end 120 of the graft delivery tube 114 may be inserted into the cavity 110 of the surgical implant 106 through the side 122 of the surgical implant 106.

Figure 3C:
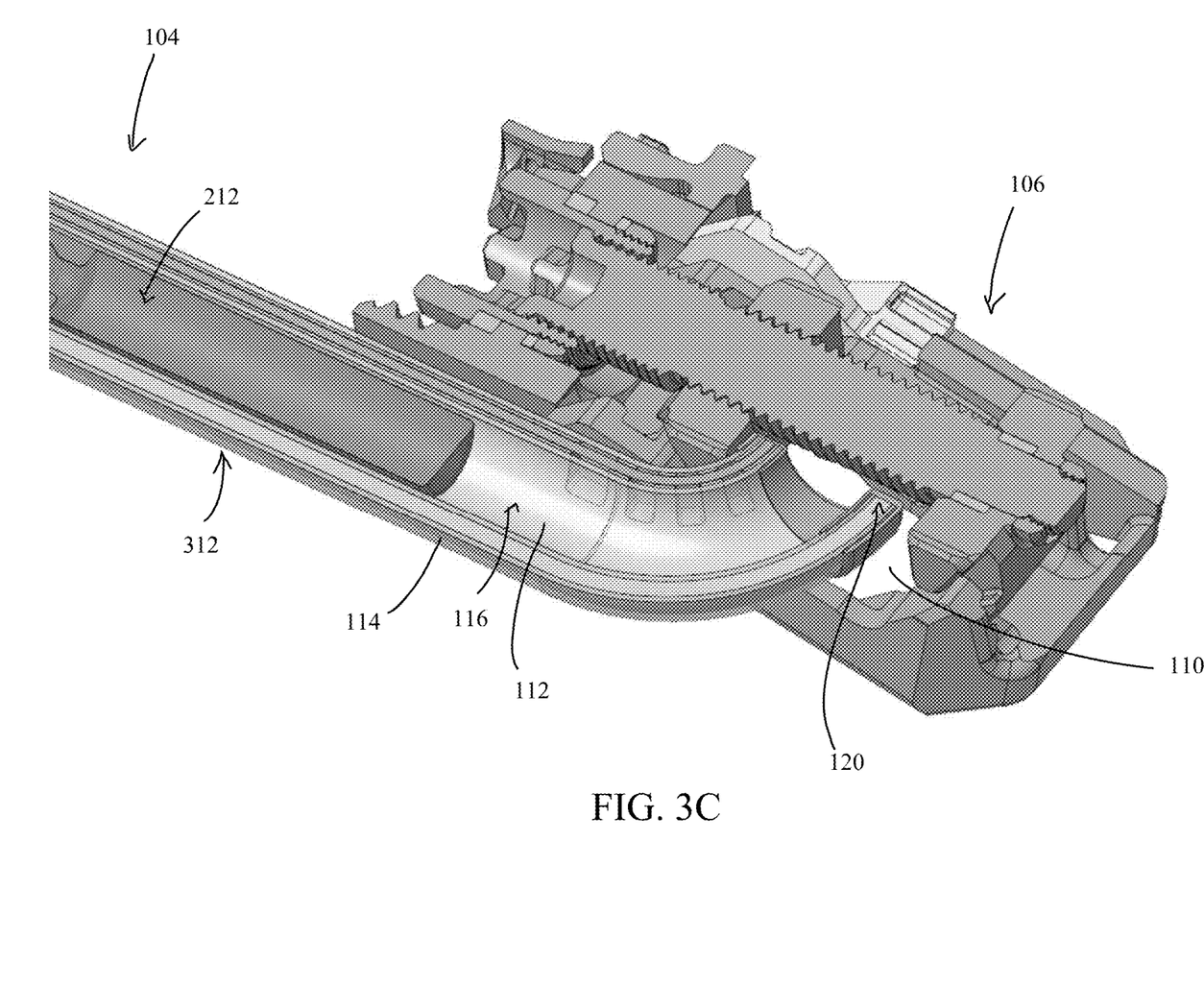
FIG. 3C is a cutaway view of the graft delivery device with the pusher device moving toward an actuated position.

FIG. 3C is a cutaway view of the graft delivery device 104 with the pusher device 212 moving toward an actuated position. With the graft delivery tube 114 in the delivery position (e.g., with the output end 120 inserted into the surgical implant 106), the graft delivery device 104 may begin to drive the graft material 112 out the output end 120 and into the cavity 110 of the surgical implant 106. The graft material 112 may be positioned in the main passage 116 of the graft delivery tube 114 between the pusher device 212 and the output end 120 of the graft delivery tube 114. As such, movement of the pusher device 212 toward the output end 120 may drive the graft material 112 toward and out of the output end 120. Moreover, in the illustrated embodiment, the pusher device 212 is positioned in a rigid or a straight portion 312 of the graft delivery tube 114.

Figure 3D:
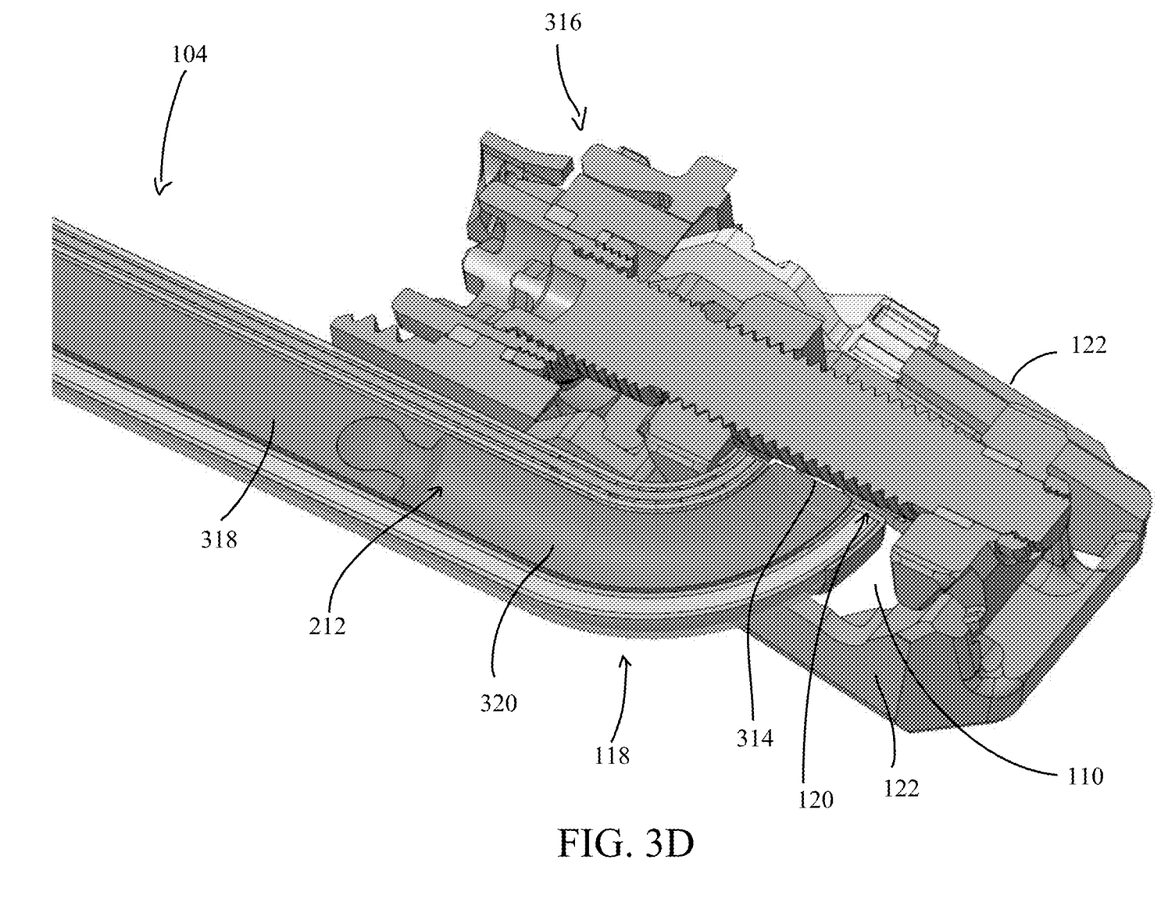
FIG. 3D is a cutaway view of the graft delivery device with the pusher device in the actuated position.

FIG. 3D is a cutaway view of the graft delivery device 104 with the pusher device 212 in the actuated position. In the actuated position, a tip end 314 of the pusher device 212 is axially aligned with the output end 120 such that the pusher device 212 drives the graft material 112, originally positioned between the pusher device 212 and the output end 120, into the cavity 110 of the surgical implant 106. As set forth above, the output end 120 of the graft delivery tube 114 delivers the graft material 112 to the surgical implant 106 through the side 122 of the surgical implant 106. The sides 122 of the surgical implant are adjacent to a front portion 316, which is interfaceable with the surgical implant inserter 102. The surgical implant inserter 102 may still be connected with the surgical implant 106 during delivery of the graft material 112. Having the graft delivery device 104 move to the articulated position allows the graft delivery device 104 to deliver the graft material 112 with the surgical implant inserter 102 either connected or disconnected with the surgical implant 106.

Moreover, the pusher device 212 slides through the articulating portion 118 of the graft delivery tube 114 to reach the actuated position. The pusher device 212 may include a pusher arm 318 and a pusher tip 320 coupled to a distal end of the pusher arm. As illustrated, the pusher tip 320 may include a flexible material such that the pusher tip 320 may bend with the curvature of the articulating portion 118 as the pusher tip 320 move through the articulating portion 118 to the actuated position.

Figure 4:
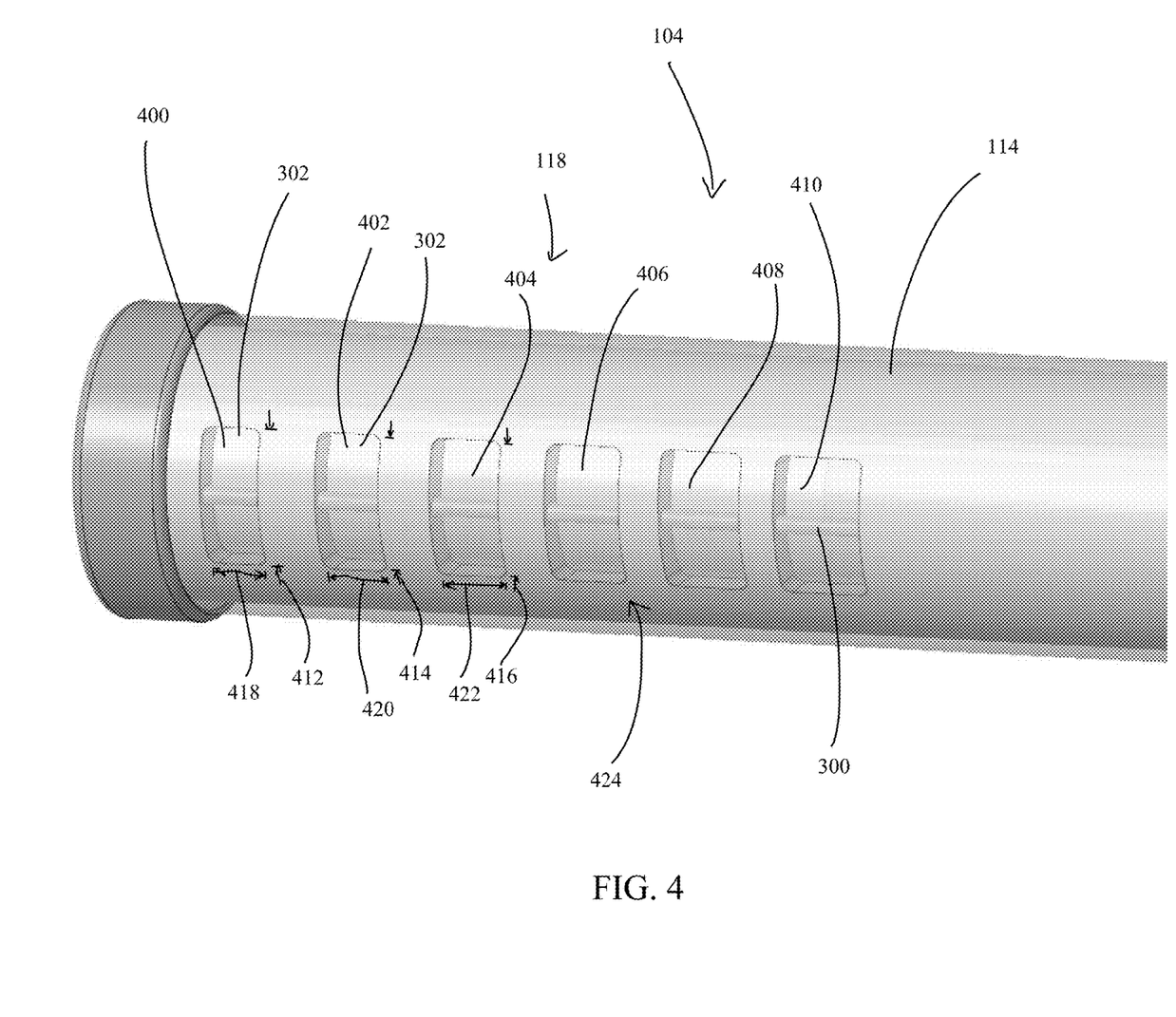
FIG. 4 is a perspective view of a graft delivery tube of the graft delivery device.

FIG. 4 is a perspective view of an example configuration of the graft delivery tube 114 of the graft delivery device 104. As illustrated, the articulating portion 118 may include a plurality of articulation slits 302 formed in the graft delivery tube 114. The plurality of articulation slits 302 may reduce a bending resistance of the articulating portion 118 such that the actuation wire 300 may require a lower amount of force to transition from the entry position to the delivery position than a graft delivery tube without the plurality of articulation slits 302. Further, the plurality of articulation slits 302 may define radii of curvature along a length of the articulating portion 118 of the graft delivery tube 114 in the articulated position (e.g., bent position) based at least in part on respective sizes, shapes, and positions of each articulation slit of the plurality of articulation slits 302.

For example, as illustrated, the graft delivery tube 114 may include a first slit 400, a second slit 402, a third slit 404, a fourth slit 406, a fifth slit 408, and a sixth slit 410. In the illustrated embodiment, the plurality of articulation slits 302 are circumferentially aligned. Alternatively, the at least one slit of the plurality of articulation slits 302 may be rotated about the graft delivery tube 114 such that the at least one slit (e.g., the first slit 400) is circumferentially offset from the remaining slits of the plurality of articulation slits 302. Moreover, in the illustrated example, the first slit 400, the second slit 402, and the third slit 404 have substantially similar circumferential widths and axial heights. That is, a first circumferential width 412 of the first slit 400 may be equal to a second circumferential width 414 of the second slit 402 and a third circumferential width 416 of the third slit 404, and a first axial height 418 of the first slit 400 may be equal to a second axial height 420 of the second slit 402 and a third axial height 422 of the third slit 404. Further, the fourth slit 406, the fifth slit 408, and the sixth slit 410 may each have a substantially similar circumferential width as the first slit 400, the second slit 402, and the third slit 404. However, the fourth slit 406, the fifth slit 408, and the sixth slit 410 may each have a substantially similar axial height that is greater than the respective axial heights of the first slit 400, the second slit 402, and the third slit 404.

Accordingly, the articulating portion 118 may bend along the fourth slit 406, the fifth slit 408, and the sixth slit 410 more than along the first slit 400, the second slit 402, and the third slit 404 in response to the actuation device 310 pulling the actuation wire 300. Indeed, as the fourth slit 406, the fifth slit 408, and the sixth slit 410 have a greater axial height, the fourth slit 406, the fifth slit 408, and the sixth slit 410 have a reduced bending resistance such that the force along the graft delivery tube 114 from pulling the actuation wire 300 may bend the fourth slit 406, the fifth slit 408, and the sixth slit 410 more than the first slit 400, the second slit 402, and the third slit 404. As such, modifying the respective axial heights of each slit of the plurality of articulation slits 302 may define the radii of curvature along a length of the articulating portion 118 of the graft delivery tube 114 in the articulated position.

As set forth above, the graft delivery tube 114 moves to the articulated position in response to the actuation device 310 (shown in FIG. 6) pulling the actuation wire 300. In the illustrated embodiment, the actuation wire 300 is circumferentially aligned with the plurality of articulation slits 302 such that the actuation wire 300 passes through each of the articulation slits. However, the actuation wire 300 may extend through any suitable portion of the graft delivery tube 114. For example, the actuation wire 300 may be disposed on an opposite side (e.g., 180-degrees offset) from the plurality of articulation slits 302. Pulling the actuation wire 300 may cause the portion of the graft delivery tube 114 circumferentially aligned with the actuation wire 300 to compress and the radii of curvature along the articulating portion 118 may be based at least in part on the plurality of articulation slits 302 disposed opposite the actuation wire 300. Indeed, to bend the articulating portion 118, the side of the graft delivery tube proximate the actuation wire 300 may compress a side of the graft delivery tube 114 opposite the actuation wire 300 may extend (e.g., stretch). As such, the plurality of articulation slits 302 on the opposite side of the graft delivery tube 114 may also reduce the bending resistance of the articulating portion 118. Further, the respective axial heights of each slit of the plurality of articulation slits 302 disposed opposite the actuation wire 300 may also define the radii of curvature along a length of the articulating portion 118 of the graft delivery tube 114 in the articulated position.

Moreover, in some embodiments, the plurality of articulation slits 302 may include a first group of slits 424 circumferentially aligned with the actuation wire 300 and a second group of slits (not shown) disposed on the opposite side (e.g., about 180-degrees offset) from the actuation wire 300 to provide additional control in defining radii of curvature along a length of the articulating portion 118 of the graft delivery tube 114 in the articulated position.

Figure 5A:
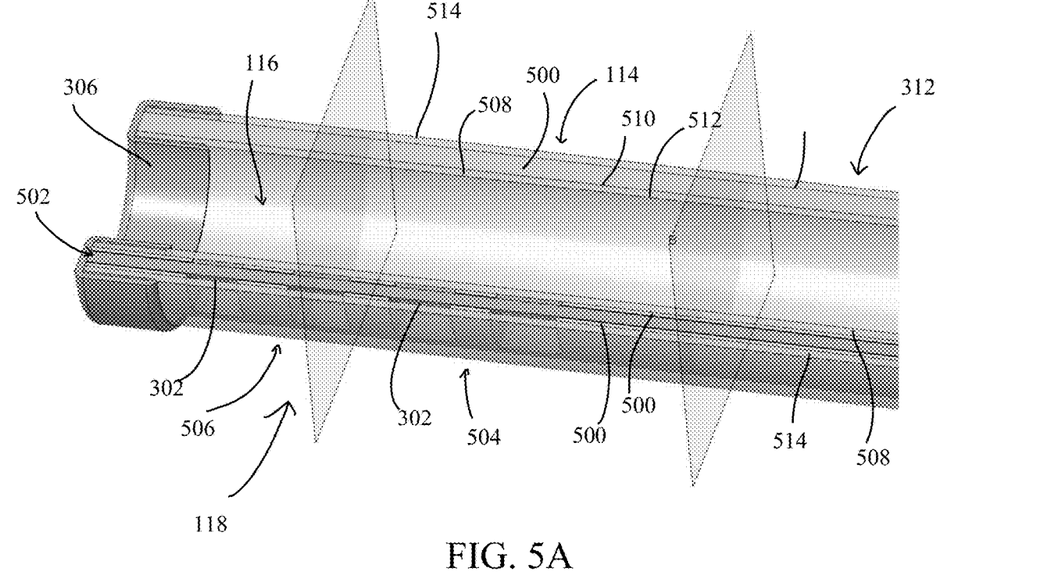
FIG. 5A is a cutaway view of the graft delivery tube and respective cross-sectional views along a length of the graft delivery tube.
Figure 5B:
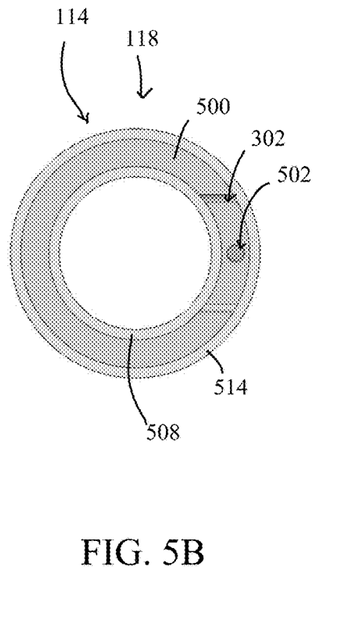
FIG. 5B is a cross-sectional view of the articulating portion of the graft delivery tube.
Figure 5C:
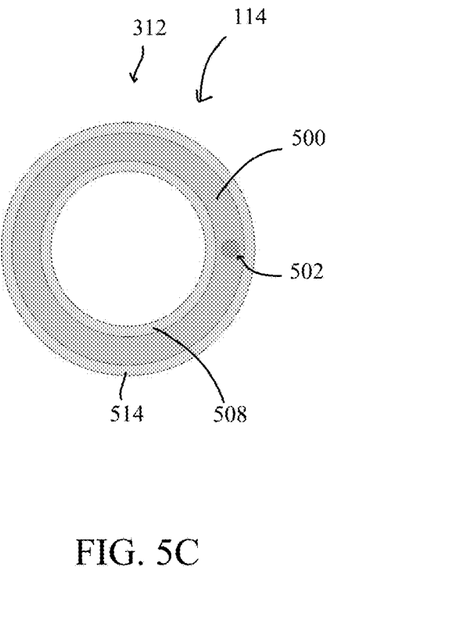
FIG. 5C is a cross-sectional view of the straight portion of the graft delivery tube.

FIGS. 5A-5C are cutaway views of the graft delivery tube 114 and respective cross-sectional views of the graft delivery tube 114. Referring to FIG. 5A, the graft delivery tube 114 includes a main structural layer 500 having a tubular shape. The main structural layer 500 may include a flexible rubber material or other suitable material. The main structural layer 500 may be sufficiently flexible such that the main structural layer 500 may bend to the articulated position. However, the main structural layer 500 may also be sufficiently rigid to maintain its cylindrical shape along the straight portion 312 and the articulating portion 118 of the graft delivery tube 114. Further, the graft delivery tube 114 includes an actuation wire passageway 502 extending axially along the length of the graft delivery tube 114 through the main structural layer 500.

Moreover, the graft delivery tube 114 includes the plurality of articulation slits 302. As illustrated, the plurality of articulation slits 302 may be formed in the main structural layer 500 in the articulating portion 118 of the graft delivery tube 114. As illustrated, each articulation slit of the plurality of articulation slits 302 may be circumferentially aligned about the main structural layer 500. Further, each articulation slit of the plurality of articulation slits 302 may be axially offset from adjacent articulation slits. The radii of curvature along the length of the articulating portion 118 of the graft delivery tube 114 in the articulated position may be based at least in part on the amount of axial offset between each articulation slit of the plurality of articulation slits 302. For example, a first section 504 of the articulating portion 118 having a smaller axial offset(s) than a second section 506 of the articulating portion 118 may have a smaller radius of curvature (e.g., bend more) than the second section 506.

The graft delivery tube 114 also includes an inner layer 508 interfaced with an inner surface 510 of the main structural layer 500. An interior surface 512 of the inner layer 508 defines the main passage 116 of the graft delivery tube 114. Further, the inner layer 508 is configured to shield the main structural layer 500 from the pusher device 212 (shown in FIG. 3D). Indeed, the inner layer 508 may be lubricious to facilitate sliding of the pusher device 212 along the main passage 116. Moreover, the main passage 116 may have a substantially similar diameter as the pusher tip 320 (shown in FIG. 3D) such that a seal is formed between the pusher tip 320 and the interior surface 512 of the inner layer 508. The seal may prevent the graft material 112 from flowing backwards past the pusher device 212 such that the pusher device 212 may drive the graft material 112 forward along the graft delivery tube 114.

Additionally, the graft delivery tube 114 includes an outer layer 514 interfaced with an exterior surface 516 of the main structural layer 500. The outer layer 514 is configured to shield or protect the main structural layer 500 from surrounding tissue and/or components during a surgical procedure. For example, the outer layer 514 may prevent fluids from entering the main passage 116, which may prevent cross-contamination between the fluids and the graft material 112. Further, the inner layer 508 and the outer layer 514 together may form a seal around the main structural layer 500, as well as the plurality of articulation slits 302. Moreover, the end cap 306 may seal the layers (e.g., the outer layer 514, the main structural layer 500, and the inner layer 508) together to prevent passage of unwanted material between the layers. The end cap 306 may also provide a radio-opaque marker for visualization under fluoroscopy.

FIG. 5B is a cross-sectional view of the articulating portion 118 of the graft delivery tube 114. As set forth above, the actuation wire passageway 502 may extend axially along the length of the graft delivery tube 114 through the main structural layer 500. Accordingly, the main structural layer 500 may have a thickness greater than a diameter of an actuation wire passageway 502 such that the actuation wire passageway 502 may be fully enclosed by the main structural layer 500. Additionally, as illustrated, the actuation wire passageway 502 may pass through at least one articulation slit of the plurality of articulation slits 302. Moreover, the main structural layer 500 may be thicker than the inner layer 508 and/or the outer layer 514 since the main structural layer 500 may be configured to provide structural rigidity for the graft delivery tube 114.

FIG. 5C is a cross-sectional view of the straight portion 312 of the graft delivery tube 114. As illustrated, the straight portion 312 of the graft delivery tube 114 includes the main structural layer 500 with the actuation wire passageway 502, as well as the inner layer 508 and the outer layer 514. However, the straight portion 312 does not include the plurality of articulation slits 302 (shown in FIG. 4) as the straight portion 312 is configured to remain straight during operation.

Figure 6:
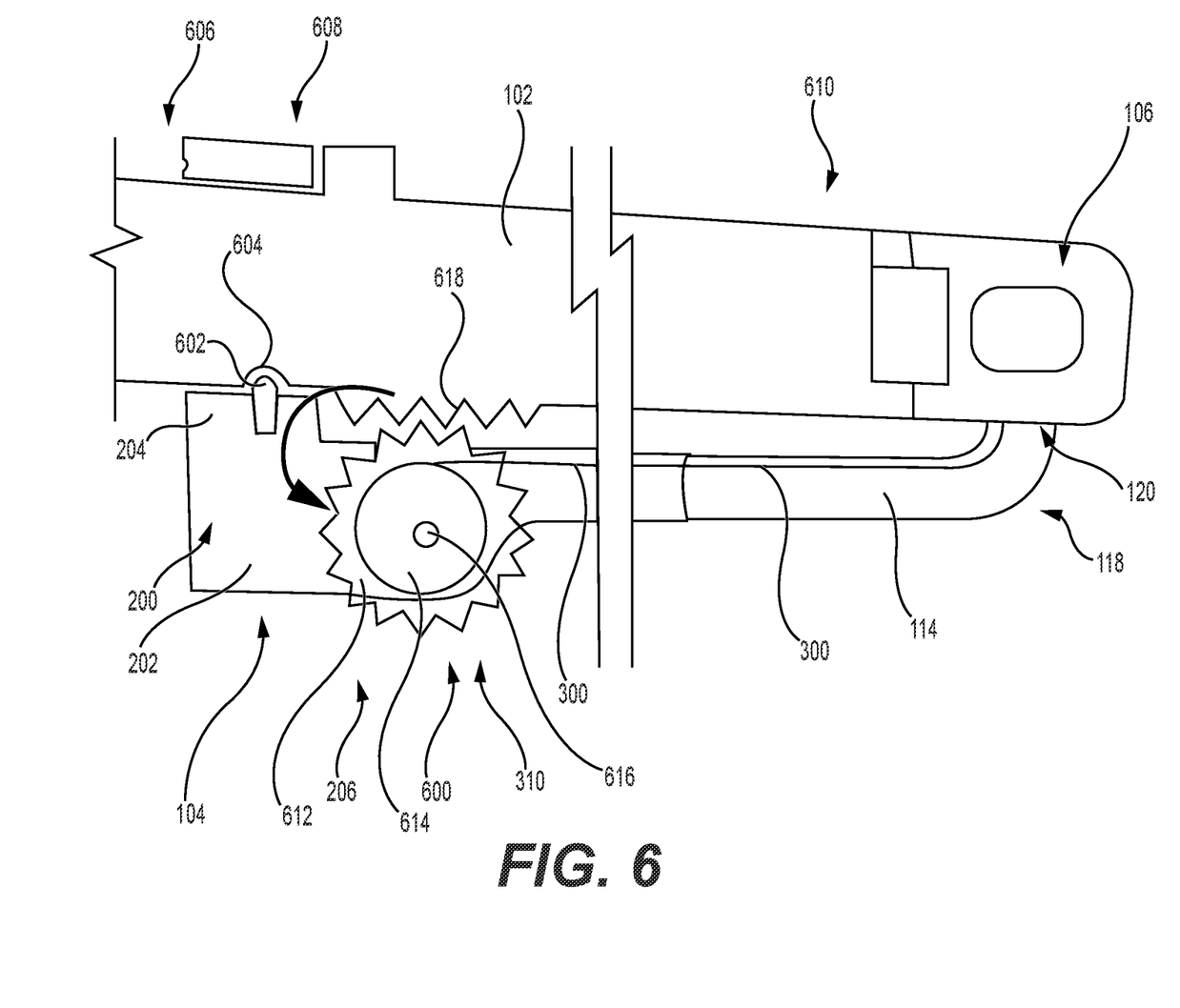
FIG. 6 is a cross-sectional view of the graft delivery device having a wheel-based actuator, in accordance with embodiments of the present disclosure.

FIG. 6 is a cross-sectional view of the graft delivery device 104 according to an example configuration having a wheel-based actuator 600. As illustrated, the actuation device may be a wheel-based actuator 600. Accordingly, the wheel-based actuator 600 may be actuatable to pull the actuation wire 300 to bend the articulating portion 118 of the graft delivery tube 114 from the entry position to the articulated position.

As illustrated, the graft delivery device 104 may include the attachment device 200 having the main body portion 202 and the coupling portion 204 for slidably coupling the graft delivery device 104 to the surgical implant inserter 102. Additionally, the main body portion 202 of the attachment device 200 is disposed around the graft delivery tube 114 proximate the input end 206 of the graft delivery tube 114. Moreover, the coupling portion 204 includes a retention feature 602 (e.g., a ball detent) engageable with a corresponding receiving feature 604 (e.g., a slot) of the surgical implant inserter 102 to restrain axial movement the attachment device 200 with respect to the surgical implant inserter 102 in the delivery position. However, in the entry position, the coupling portion 204 may slide along the surgical implant inserter 102.

For example, the coupling portion 204 may be slid over the surgical implant inserter 102 near a proximal end 606 of an inserter sleeve 608 of the surgical implant inserter 102. With the coupling portion 204 disposed about the inserter sleeve 608 in the entry position, the coupling portion 204 may slide forward toward the distal end 610 of the surgical implant inserter 102. As the coupling portion 204 of the attachment device slides forward into the delivery position, the retention feature 602 may engage the receiving feature 604 to lock axial movement (e.g., sliding) of the coupling portion 204 with respect to the inserter sleeve 608.

The actuation device 310 (e.g., the wheel-based actuator 600) may be secured to the main body portion 202 of the attachment device 200. As the coupling portion 204 slides forward, the main body portion 202 may also slide forward. Such movement may cause the actuation device 310 to pull the actuation wire 300. In particular, the wheel-based actuator 600 may include a pinion wheel 612 secured to the graft delivery device 104 via an actuation hub 614 mounted to the main body portion 202 of the attachment device 200. The actuation hub 614 may include a pivot shaft 616, and the pinion wheel 612 may be mounted to the graft delivery device 104 via the pivot shaft 616. Further, the pinion wheel 612 may rotate about the pivot shaft 616. However, the wheel-based actuator 600 may be secured to the graft delivery device 104 via any suitable components.

Moreover, the pinion wheel 612 may also be connected to the actuation wire 300. As the coupling portion 204 slides forward, the pinion wheel 612 may also slide forward with the main body portion 202 to interface with a rack 618 formed on the surgical implant inserter 102. The engagement with the rack 618, in response to the axial movement of the pinion wheel 612, may drive rotation of the pinion wheel 612. Rotation of the pinion wheel 612 pulls the actuation wire 300 to bend the articulating portion 118 of the graft delivery tube 114 and position the output end 120 of the graft delivery tube 114 proximate the surgical implant 106.

Figure 7:
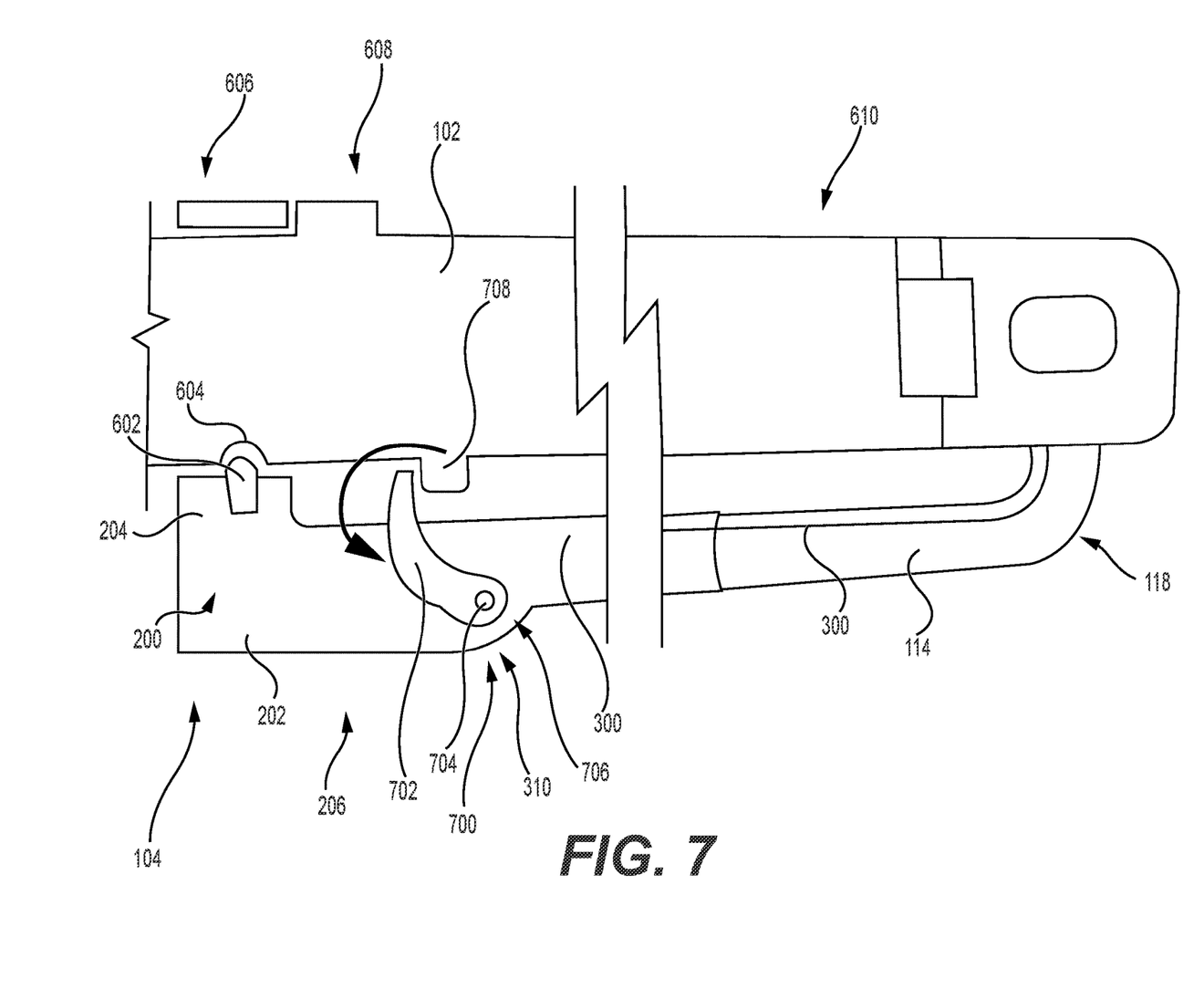
FIG. 7 is a cross-sectional view of the graft delivery device having a trigger actuator.

FIG. 7 is a cross-sectional view of the graft delivery device 104 according to an example configuration having a trigger actuator 700. As illustrated, the actuation device 310 may be a trigger actuator 700. As such, the trigger actuator 700 may be actuatable to pull the actuation wire 300 to bend the articulating portion 118 of the graft delivery tube 114 from the entry position to the articulated position.

As set forth above, the graft delivery device 104 may include the attachment device 200 having the main body portion 202 and the coupling portion 204 for slidably coupling the graft delivery device 104 to the surgical implant inserter 102. Additionally, the main body portion 202 of the attachment device 200 is disposed around the graft delivery tube 114 proximate the input end 206 of the graft delivery tube 114. Moreover, the coupling portion 204 may include the retention feature 602 (e.g., a ball detent) engageable with the corresponding receiving feature 604 (e.g., a slot) of the surgical implant inserter 102 to restrain axial movement the attachment device 200 with respect to the surgical implant inserter 102 in the delivery position. However, in the entry position, the coupling portion 204 may slide along the surgical implant inserter 102. For example, the coupling portion 204 may be slid over the surgical implant inserter 102 near the proximal end 606 of the inserter sleeve 608 of the surgical implant inserter 102. With the coupling portion 204 disposed about the inserter sleeve 608 in the entry position, the coupling portion 204 may slide forward toward the distal end 610 of the surgical implant inserter 102. As the coupling portion 204 of the attachment device 200 slides forward into the delivery position, the retention feature 602 may engage the receiving feature 604 to lock axial movement (e.g., sliding) of the coupling portion 204 with respect to the inserter sleeve 608.

The actuation device 310 (e.g., the trigger actuator 700) may be secured to the main body portion 202 of the attachment device 200. As the coupling portion 204 slides forward, the main body portion 202 may also slide forward. Such movement may cause the trigger actuator 700 to pull the actuation wire 300. In particular, the trigger actuator 700 may include a trigger arm 702 secured to the graft delivery device 104 via a pivot joint 704 disposed at a pivot end 706 of the trigger arm 702. Further, the surgical implant inserter 102 may include an actuation shoulder 708 formed on the surgical implant inserter 102. As the trigger actuator 700 slides axially forward toward the delivery position, via movement of the main body portion 202, the trigger arm 702 may be driven into the actuation shoulder 708 to actuate the trigger actuator 700. Specifically, the trigger arm 702 is configured to rotate about the pivot joint 704 in response to contact with an actuation shoulder 708 of a surgical implant inserter 102. As the actuation wire 300 is secured to the trigger arm 702, such that rotation of the trigger arm 702 pulls the actuation wire 300 to bend the articulating portion 118 of the graft delivery tube 114 from the entry position to the articulated position.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Various advantages of the present disclosure have been described herein, but embodiments may provide some, all, or none of such advantages, or may provide other advantages.

What is claimed is:

1. A graft delivery device, comprising:
a graft delivery tube having a main passage for delivering graft material to a surgical implant inserted between adjacent vertebrae of a spine and an articulating portion proximate an output end of the graft delivery tube;
a pusher device slidable along the main passage to drive graft material through the main passage toward the output end of the graft delivery tube;
an actuation wire extending axially through at least the articulating portion of the graft delivery tube; and
an actuation device connected to the actuation wire, wherein the actuation device is actuatable to pull the actuation wire to bend the articulating portion of the graft delivery tube and position the output end proximate the surgical implant,
an attachment device having a main body portion and a coupling portion for slidably coupling the graft delivery device to a surgical implant inserter, and wherein the main body portion of the attachment device is disposed around the graft delivery tube proximate an input end of the graft delivery tube.

2. The graft delivery device of claim 1, wherein the coupling portion comprises a retention feature engageable with a corresponding receiving feature of the surgical implant inserter to restrain axial movement of the attachment device with respect to the surgical implant inserter, and wherein the retention feature comprises a ball detent.

3. The graft delivery device of claim 1, wherein the actuation device is secured to the main body portion of the attachment device.

4. The graft delivery device of claim 1, wherein the actuation device comprises a trigger arm secured to the graft delivery device via a pivot joint disposed at a pivot end of the trigger arm, wherein the trigger arm is configured to rotate about the pivot joint in response to contact with an actuation shoulder of a surgical implant inserter, and wherein the actuation wire is secured to the trigger arm such that rotation of the trigger arm pulls the actuation wire.

5. The graft delivery device of claim 4, further comprising an endcap disposed at the output end of the graft delivery tube, and wherein the actuation wire comprises a first end secured by the endcap proximate the output end and a second end secured to the trigger arm of the actuation device such that movement of the trigger arm pulls the actuation wire.

6. The graft delivery device of claim 1, wherein the graft delivery tube moves to the bent position in response to the actuation device pulling the actuation wire, and wherein the graft delivery tube comprises a plurality of articulation slits, wherein the plurality of articulation slits define radii of curvature along a length of the articulating portion of the graft delivery tube in a bent position based at least in part on respective sizes, shapes, and positions of each articulation slit of the plurality of articulation slits.

7. The graft delivery device of claim 6, wherein the actuation wire is circumferentially aligned with the plurality of articulation slits such that the actuation wire passes through the articulation slits at axial locations of the articulation slits.

8. The graft delivery device of claim 1, wherein the graft delivery tube comprises:
   a main structural layer having a tubular shape;
   an actuation wire passageway extending axially through the main structural layer;
   a plurality of articulation slits formed in the main structural layer along the articulating portion of the graft delivery tube;
   an inner layer interfaced with an inner surface of the main structural layer, wherein an interior of the inner layer defines the main passage of the graft delivery tube; and
   an outer layer interfaced with an exterior surface of the main structural layer, wherein the inner layer and the outer layer enclose the plurality of articulation slits.

9. The graft delivery device of claim 8, wherein each articulation slit of the plurality of articulation slits are circumferentially aligned about the main structural layer, and wherein each articulation slit of the plurality of articulation slits are axially offset from adjacent articulation slits.

10. The graft delivery device of claim 8, wherein the actuation wire extends axially through the actuation wire passageway formed in the main structural layer of the graft delivery tube.

11. The graft delivery device of claim 1, wherein the pusher comprises a pusher arm and a pusher tip coupled to a distal end of the pusher arm, and wherein the pusher tip comprises a flexible material.

12. The graft delivery device of claim 11, wherein a proximal end of the pusher arm extends out of a rigid end of the graft delivery tube, and wherein the proximal end of the pusher arm comprises a handle.

13. The graft delivery device of claim 1, wherein the graft delivery tube moves to a bent position in response to the actuation device pulling the actuation wire to bend the articulating portion of the graft delivery tube, and the output end of the graft delivery tube is inserted into the surgical implant through a sidewall of the surgical implant.

14. A graft delivery device, comprising:
   a graft delivery tube having a main passage for delivering graft material to a surgical implant inserted between adjacent vertebrae of a spine, wherein the graft delivery tube includes an articulating portion proximate an output end of the graft delivery tube;
   a pusher device slidable along the main passage to drive graft material through the main passage toward the output end of the graft delivery tube;
   an actuation wire extending axially through at least the articulating portion of the graft delivery tube; and
   a pinion wheel secured to the graft delivery device and connected to the actuation wire, wherein the pinion wheel is configured to interface with a rack formed on a surface of a surgical implant inserter, wherein the pinion wheel rotates in response to axial movement of the graft delivery device with respect to a surgical implant inserter, and wherein rotation of the pinion wheel pulls the actuation wire to bend the articulating portion of the graft delivery tube and position the output end of the graft delivery tube proximate the surgical implant.

15. The graft delivery device of claim 14, further comprising an attachment device having a main body portion and a coupling portion for slidably coupling the graft delivery device to a surgical implant inserter, and wherein the main body portion of the attachment device is disposed around the graft delivery tube proximate an input end of the graft delivery tube.

16. The graft delivery device of claim 15, further comprising an actuation hub mounted to the main body portion of the attachment device, wherein the hub comprises a pivot shaft, and wherein the pinion wheel is mounted to the graft delivery device via the pivot shaft, and wherein the pinion wheel rotates about the pivot shaft.

17. The graft delivery device of claim 14, wherein the output end of the graft delivery tube delivers the graft material to the surgical implant through a side portion of the surgical implant, wherein the side portion of the surgical implant is adjacent to a front portion interfaceable with a surgical implant inserter.

18. A surgical implant system, comprising:
   a surgical implant inserter for placing a surgical implant between adjacent vertebrae of a spine; and
   a graft delivery device couplable to the surgical implant inserter, wherein the graft delivery device comprises:
      a graft delivery tube having a main passage for delivering graft material to a surgical implant inserted between adjacent vertebrae of a spine and an articulating portion proximate an output end of the graft delivery tube;
      a pusher device slidable along the main passage to drive graft material through the main passage toward the output end of the graft delivery tube;
      an actuation wire extending axially through at least the articulating portion of the graft delivery tube; and
      an actuation device connected to the actuation wire, wherein actuating the actuation device pulls the actuation wire to bend the articulating portion of the graft delivery tube and position the output end proximate the surgical implant,
   wherein the surgical implant inserter comprises an actuation shoulder formed on an outer surface of the surgical implant inserter, wherein the graft delivery device is configured to slide axially along the surgical implant inserter to drive the actuation device into the actuation shoulder to actuate the actuation device.

* * * * *